United States Patent
Frischke et al.

(10) Patent No.: US 12,144,974 B2
(45) Date of Patent: Nov. 19, 2024

(54) CONTROL DEVICE FOR AN IMPLANTABLE HEART PUMP

(71) Applicant: Berlin Heart GmbH, Berlin (DE)

(72) Inventors: Michael Frischke, Rangsdorf (DE); Sebastian Kallenbach, Kassel (DE)

(73) Assignee: Berlin Heart GmbH, Berlin (DE)

( * ) Notice: Subject to any disclaimer, the term of this patent is extended or adjusted under 35 U.S.C. 154(b) by 846 days.

(21) Appl. No.: 16/468,938

(22) PCT Filed: Dec. 13, 2017

(86) PCT No.: PCT/EP2017/082687
§ 371 (c)(1),
(2) Date: Dec. 3, 2019

(87) PCT Pub. No.: WO2018/109038
PCT Pub. Date: Jun. 21, 2018

(65) Prior Publication Data
US 2020/0222605 A1    Jul. 16, 2020

(30) Foreign Application Priority Data
Dec. 14, 2016   (EP) ..................................... 16204167

(51) Int. Cl.
*A61M 60/165*   (2021.01)
*A61M 60/148*   (2021.01)
(Continued)

(52) U.S. Cl.
CPC ........ *A61M 60/148* (2021.01); *A61M 60/178* (2021.01); *A61M 60/183* (2021.01);
(Continued)

(58) Field of Classification Search
CPC .. A61N 1/36125; A61M 60/50; A61M 60/871
See application file for complete search history.

(56) References Cited

U.S. PATENT DOCUMENTS

| 5,571,141 A | * | 11/1996 | McNeil | ................ A61N 1/3706 |
| | | | | 607/5 |
| 2007/0173898 A1 | | 7/2007 | Ayre et al. | |
| 2012/0078031 A1 | | 3/2012 | Burke et al. | |
| 2013/0006326 A1 | * | 1/2013 | Ackermann | ......... A61N 1/3606 |
| | | | | 607/53 |

(Continued)

OTHER PUBLICATIONS

International Search Report, issued in International Application No. PCT/EP2017/082687, dated Apr. 4, 2018, pp. 1-4, European Patent Office, Rijswijk, Netherlands.

(Continued)

*Primary Examiner* — Michael J D'Abreu
(74) *Attorney, Agent, or Firm* — Crowell & Moring LLP (57) ABSTRACT

A control apparatus for an implantable heart pump is provided, which comprises an implantable first control unit, which is electrically connected to the heart pump in a main operating state for controlling operating parameters of the heart pump. The control apparatus also comprises an interface, which is electrically connected to the first control unit and is intended to wirelessly transcutaneously transmit data and/or to wirelessly transcutaneously transmit energy between the first control unit and a further control unit provided for extracorporeal use. The control apparatus also comprises an implantable second control unit, which is electrically connected to the heart pump in an auxiliary operating state for controlling operating parameters of the heart pump, and an implantable switch, which is electrically connected to the first control unit and the second control unit. The switch is set up to change over between the main operating state and the auxiliary operating state.

16 Claims, 4 Drawing Sheets

(51) Int. Cl.
    *A61M 60/178*      (2021.01)
    *A61M 60/183*      (2021.01)
    *A61M 60/216*      (2021.01)
    *A61M 60/411*      (2021.01)
    *A61M 60/538*      (2021.01)
    *A61M 60/873*      (2021.01)
    *A61M 60/876*      (2021.01)

(52) U.S. Cl.
    CPC ........ *A61M 60/216* (2021.01); *A61M 60/411* (2021.01); *A61M 60/538* (2021.01); *A61M 60/873* (2021.01); *A61M 60/876* (2021.01); *A61M 2205/16* (2013.01); *A61M 2205/18* (2013.01); *A61M 2205/3365* (2013.01); *A61M 2205/3523* (2013.01); *A61M 2205/8206* (2013.01)

(56) References Cited

U.S. PATENT DOCUMENTS

| 2014/0243970 | A1 | | 8/2014 | Yanai |
| 2014/0324165 | A1 | | 10/2014 | Burke |
| 2015/0031938 | A1 | * | 1/2015 | Crosby ................. A61M 60/00 600/16 |
| 2015/0174309 | A1 | * | 6/2015 | Yomtov ............... A61B 5/0015 600/16 |
| 2016/0095968 | A1 | | 4/2016 | Rudser |

OTHER PUBLICATIONS

Chinese Office Action with English translation for Chinese Patent application No. 201780077100.6, dated Aug. 4, 2021, pp. 1-18, China National Intellectual Property Administration, Beijing, People's Republic of China.

* cited by examiner

CONTROL DEVICE FOR AN IMPLANTABLE HEART PUMP

CROSS-REFERENCE TO RELATED APPLICATIONS

This application is a 371 nationalization of international patent application PCT/EP2017/082687 filed Dec. 13, 2017, which claims priority under 35 USC § 119 to European patent application 16 204 167.7 filed Dec. 14, 2016. The entire contents of each of the above-identified applications are hereby incorporated by reference.

TECHNICAL FIELD

The present application resides in the field of medical technology and relates to a control device for an implantable heart pump. The present application further relates to a method for operating such a control device.

DETAILED DESCRIPTION

Implantable heart pumps for assisting a human heart are known from the prior art. Such heart pumps are configured, for example, to deliver blood from a ventricle into the aorta or into the pulmonary artery and can be designed, for example, as a so-called left ventricular assist device (LVAD), right ventricular assist device (RVAD) or bi-ventricular assist device (BiVAD). In typical designs, an electric energy supply system and a control unit for the heart pump are provided, which are disposed outside the body and connected to the heart pump via at least one transcutaneous line. In the event that a fault occurs in the control unit, a patient using the implantable heart pump typically carries along a replacement control unit at all times. The control unit is usually configured to generate an alarm if a fault occurs therein. The alarm prompts the patient to exchange the control unit with the replacement control unit. So as to allow the patient to carry out an exchange of the control units within a short time, the patient is usually specially trained.

In the above-described systems, a passage point through the skin is needed for supplying energy to and controlling the heart pump, thereby increasing a risk of infection in the patient. As a result, endeavors are being made, for example, to design the control unit of the heart pump so as to be implantable, and to supply the heart pump and/or the control unit wirelessly and transcutaneously with energy (so-called transcutaneous energy transfer, TET). A use of such a system, however, is associated with the disadvantage that the implanted control unit cannot be readily exchanged by the patient for a replacement control unit when a fault of the control unit occurs.

It is therefore the object of the present application to propose an improved control device for an implantable heart pump, which overcomes the disadvantages of above-described systems. In particular, it is an object of the present application to propose a control device that is characterized by an enhanced fault-secure design and a low risk of infection for the patient.

The proposed control device for an implantable heart pump comprises an implantable first control unit, which in a main operating state can be electrically connected, and preferably is electrically connected, to the heart pump for controlling operating parameters of the heart pump. Moreover, the control device comprises an interface that can be electrically connected, and preferably is electrically connected, to the first control unit for the wireless, transcutaneous data transmission and/or for the wireless, transcutaneous energy transmission between the first control unit and a further control unit provided for extracorporeal use. The control device moreover comprises an implantable second control unit, which in an auxiliary operating state can be electrically connected, and preferably is electrically connected, to the heart pump for controlling operating parameters of the heart pump, and an implantable switch that can be electrically connected, and preferably is electrically connected, to the first control unit and the second control unit. The switch is configured to switch between the main operating state and the auxiliary operating state. Switching is preferably initiated by one of the first control unit and second control unit and can be carried out without human intervention. The operating parameters of the heart pump can encompass or consist of a driving speed and/or a rotor speed and/or a motor current, for example. In addition, the operating parameters can also be signals for activating sensors. For example, it may be provided that the sensors are deactivated or, for example, operated at a lower power in the auxiliary operating state.

The application moreover relates to a heart pump device comprising a control device as described above and/or hereafter and a heart pump electrically connected to the switch. Moreover, the present application relates to a system comprising a control device as described above and/or hereafter or a heart pump device as described above and/or hereafter. The system can moreover comprise the further control unit which is provided for extracorporeal use.

The switch can be configured to switch from the main operating state into the auxiliary operating state as a result of a malfunction and/or a failure of the first control unit. In this way, the proposed control device ensures that the heart pump continues to be operated by the second control unit even in the event of a malfunction or the failure of the first control unit. A patient using the heart pump device is thus given sufficient time to seek medical assistance in the event of a failure of the first control unit. Thereafter, a surgical procedure can be carried out to exchange the control device or at least the first control unit.

In order to identify the malfunction and/or the failure of the first control unit, it may be provided that a keep-alive signal is transmitted, for example continuously or periodically, to a switch controller of the switch. If this keep-alive signal is absent, it may be provided that the switch switches from the main operating state into the auxiliary operating state.

In addition, or as an alternative, the first control unit or another monitoring unit of the control device could, for example permanently, monitor a current of the first control unit. If this current exceeds or drops below an established limit value, the switch switches from the main operating state into the auxiliary operating state. It may additionally be provided that the first control unit shuts off in the auxiliary operating state. In addition, or as an alternative, it may also be provided that the first control unit or the monitoring unit monitors a temperature of the first control unit. If the temperature of the first control unit exceeds an established limit value, the switch can switch from the main operating state into the auxiliary operating state switch.

Since both the first control unit and the second control unit are designed to be implantable and the control device comprises the interface for transcutaneous transmission, the heart pump device can be operated without necessitating a passage point through the skin for a percutaneous connecting line to supply energy to and control the pump. As a result, a risk of infection can be lowered for the patient. In other exemplary embodiments, the first control unit and the second control unit can comprise an interface for transcutaneous transmission.

In the main operating state, the second control unit is typically not electrically connected to the heart pump. It may be provided that the second control unit is disconnected from the heart pump in the main operating state, and in particular is galvanically isolated and/or de-energized. Moreover, in the auxiliary operating state the first control unit is typically not electrically connected to the heart pump. It may be provided that the first control unit is disconnected from the heart pump in the auxiliary operating state, and in particular is galvanically isolated and/or de-energized. Corresponding disconnections of the electrical connections can be carried out by the switch. For example, the switch can comprise a relay or a transistor as a switching unit. Typically, the switch comprises a switch controller, which is connected to the switching unit and controls the switching unit. The switch controller is typically designed as a logic circuit. The switch controller can be connected to the first control unit for detecting a malfunction or a failure thereof. The switch controller is typically configured to trigger a switching of the switch as a result of the malfunction or the failure, so as to cause a switch from the main operating state into the auxiliary operating state.

It may be provided that the first control unit and the second control unit are disposed in a single housing having an outer surface made of biocompatible material, whereby no further implantable component is required for the second control unit. However, it may also be provided that the first control unit and the second control unit are disposed in respective housings having outer surfaces made of biocompatible material. The housings can comprise a biocompatible shell and/or a biocompatible coating.

The first control unit can be configured to send a switching signal to the switch. Moreover, the switch can be configured to switch into the auxiliary operating state, or to maintain the auxiliary operating state, when the switching signal is absent. In this way, it is ensured that the switch, in the event of a failure of the first control unit, reliably switches into the auxiliary operating state, if the absence of the switching signal occurs in the process.

The control device can comprise an implantable main power supply unit and an implantable auxiliary power supply unit. The main power supply unit can be configured to supply the first control unit with energy. Moreover, the auxiliary power supply unit can be configured to supply the second control unit with energy. In this way, it is ensured that, even in the event of a failure of the auxiliary power supply unit or of the main power supply unit, either the second control unit or the first control unit is supplied with electric energy, and that the heart pump remains functional. It may be provided that the main power supply unit and the auxiliary power supply unit are spatially separated from one another, and in particular are disposed in different implantable housings. For example, the main power supply unit or the auxiliary power supply unit can be arranged so as to be reachable particularly easily during surgery for the exchange, for example after a number of maximum charging cycles has been reached.

In addition, or as an alternative, an implantable power supply unit can be provided, which is configured to supply both the first control unit and the second control unit with energy. A compact design of the control device can be achieved by being able to supply the first and second control units with electric energy from the same power supply unit.

An electrical connection between the power supply unit and the first control unit can be disconnectable in the auxiliary operating state, and in particular galvanically isolatable and/or de-energizable. In this way, it can be prevented that the first control unit drains the power supply unit in the auxiliary operating state, so that a long service life of the control device in the auxiliary operating state is ensured. The electrical connection between the power supply unit and the first control unit can be disconnected as a result of a switch or during a switch from the main operating state into the auxiliary operating state.

The interface typically comprises a transmitter and/or receiver coil. In some embodiments, the interface can additionally or alternatively comprise a radio antenna. In typical embodiments, the power supply unit or the main power supply unit and/or the auxiliary power supply unit are rechargeable. Typically, the power supply unit or the main power supply unit and/or the auxiliary power can be wirelessly recharged via the interface. In this way, it is possible to ensure operation of an implanted heart pump device over a long period of time. In typical embodiments, the power supply unit, the main power supply unit and/or the auxiliary power supply unit are designed as batteries or rechargeable batteries.

The switch and/or the first control unit and/or the second control unit can be designed in such a way that a switch from the main operating state into the auxiliary operating state can be triggered via a wireless and transcutaneous connection. For example, a switch into the auxiliary state can be triggerable by a magnet approaching the switch and/or the first control unit and/or the second control unit. For this purpose, the control device can comprise a reed switch, for example. The auxiliary operating state can thus be manually triggered by a user, for example when an automatic detection of a failure or of a malfunction of the first control unit fails.

In some embodiments, for example, it may be provided that the control device does not comprise any interfaces that are electrically connected to the first control unit and/or to the second control unit for an exclusively wired connection between the further control unit and the control device.

The present application also relates to a method for operating a heart pump device as described above or hereafter or a control device as described above or hereafter. The switch switches from the main operating state into the auxiliary operating state as a result of the malfunction and/or the failure of the first control unit in the process.

In typical embodiments, the heart pump is operated at a lower power in the auxiliary operating state than in the main operating state. It may also be provided that the sensors are deactivated or operated at a lower power in the auxiliary operating state. For example, it may be provided that the heart pump is operated at a constant rotor speed in the auxiliary operating state. Moreover, it may be provided that, in the main operating state, the operating parameters of the heart pump are controlled based on a sensor signal. It may also be provided that the operating parameters are controlled independently from this sensor signal in the auxiliary operating state. As a result of each of these embodiments, a particularly compact design of the second control unit is possible. Moreover, it can be achieved that an energy requirement of the control device is reduced in the auxiliary state. In this way, it can be achieved that the control device has a sufficiently long service life in the auxiliary state, so that the patient can receive medical assistance in time before failure of the heart pump.

For the detection of the sensor signal, the heart pump or the heart pump device can comprise one sensor or multiple sensors, or the sensors that were already described above. Typically, this sensor is, or these sensors are, electrically connected to the first control unit. The sensor or the sensors can comprise a selection of the following sensor types: position sensor for a rotor of the heart pump, position and/or acceleration sensor, volumetric flow sensor, temperature sensor, pressure sensor, pressure difference sensor, oxygen saturation sensor, flow sensor, or chemical sensor for blood analysis.

A compact design of the control device allows a high degree of geometric design freedom. For example, an implantable pump housing can be provided, in which the heart pump and the second control unit can be accommodated. It may also be provided that the switch is accommodated in the pump housing.

In some embodiments, it is also possible for the first control unit and the switch to be accommodated in the same housing. In this way, a particularly compact design can be achieved. This applies, in particular, when the second control unit is also accommodated in this housing. Typically, only two implantable housings are required for a heart pump device, which can accommodate the heart pump, the first control unit, the second control unit and the switch. In this way, it is also possible to reduce the number of intracorporeal connecting lines that are needed.

In typical embodiments, a housing accommodating the first control unit and/or the second control and the pump housing are connected to one another by a subcutaneous connection (driveline), which has a length of at least 15 cm and/or no more than 50 cm. So as to dispose the heart pump device in a patient's body, this subcutaneous connection is typically flexible.

It may also be provided that the control device is configured to output an alarm signal in the event of a failure of the first control unit and/or of the second control unit. In this case, the corresponding component can be exchanged by a surgical procedure.

In addition, an extracorporeal energy supply unit, such as a battery, can be provided. It may be provided that the heart pump, during operation, is supplied with electric energy by the extracorporeal energy supply unit. It may be provided that the energy is transmitted by a wireless transcutaneous connection. For this purpose, the control device can comprise an energy receiver coil. In addition, the interface can also be configured to receive energy from the extracorporeal energy supply unit. In some embodiments, however, it may also be provided that the heart pump is supplied with electric energy by the implantable power supply unit and/or the main power supply unit and/or the auxiliary power supply unit, at least for short time intervals. This can, in particular, be provided when an extracorporeal energy transmitter coil, which is connected to the extracorporeal energy supply unit and inductively coupled to the energy receiver coil, is temporarily removed for the time interval, for example during a time for the patient's personal hygiene.

Exemplary embodiments will be described hereafter based on the figures.

Figure 1:
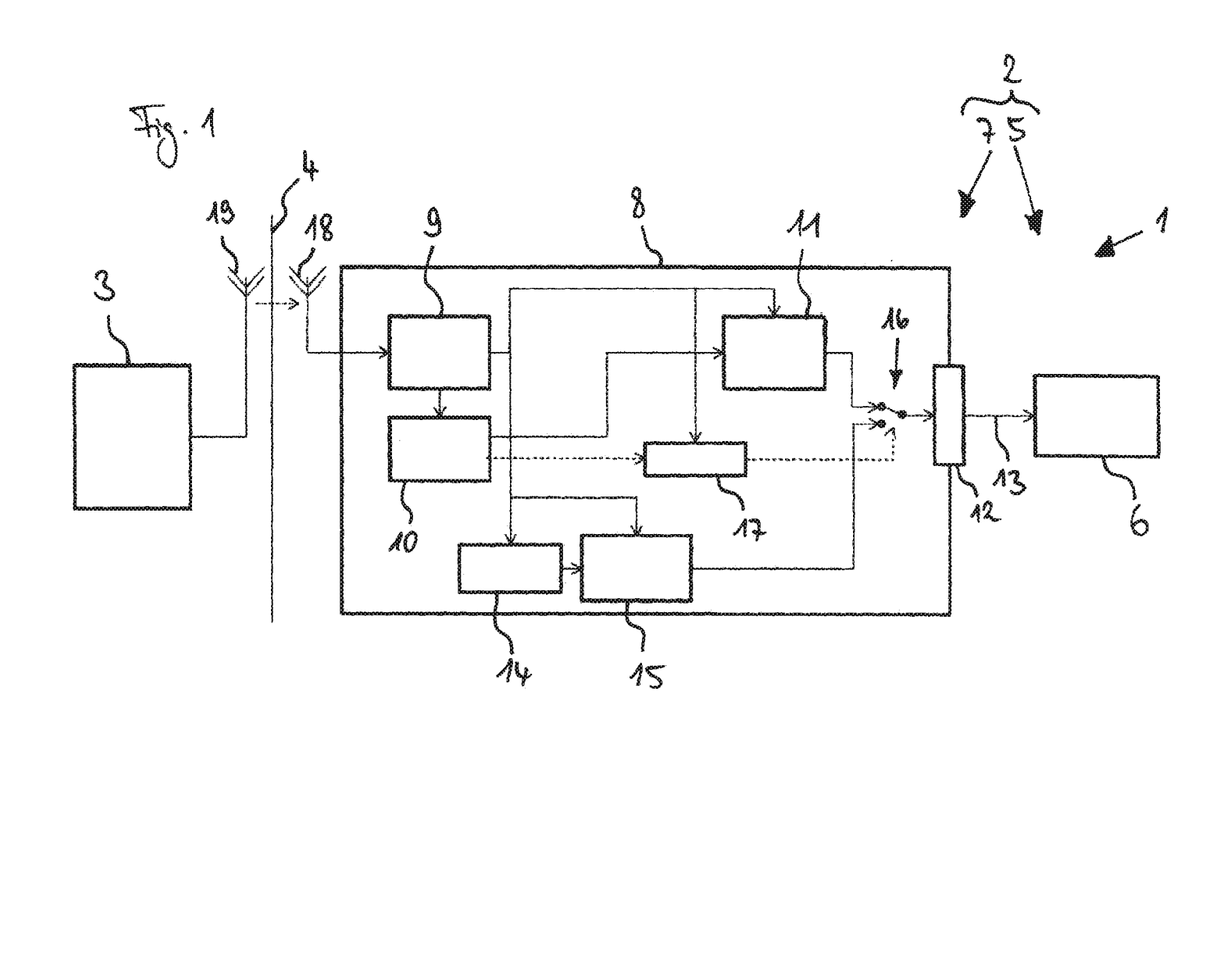
FIG. 1 shows a schematic view of a system comprising a heart pump device and a further control unit according to a first embodiment.

FIG. 1 shows a system 1 comprising an implanted heart pump device 2 and an extracorporeal control unit 3. A skin surface is shown schematically by a line denoted by reference numeral 4, wherein an interior of the body shall be understood to mean a region located to the right of the skin surface 4 and an exterior shall be understood to mean a region located to the left of the skin surface 4.

The heart pump device 2 comprises a heart pump 5. The heart pump 5 comprises at least one motor, which is disposed in an implantable, biocompatible pump housing 6 welded together in a fluid-tight manner, and a rotor driven by the motor and can be disposed in such a way that a rotation of the rotor delivers blood from the left ventricle into the aorta (so-called LVAD).

The heart pump device 2 moreover comprises a control device 7. The control device 7 is implantable and, for example, comprises a biocompatible housing 8 welded together in a fluid-tight manner. The control device 7 is connected to the heart pump 5 via a pump interface 12 and an intracorporeal driveline 13. In the shown example, a power supply unit 9 in the form of a rechargeable battery is disposed in the housing 8. Moreover, a first control unit comprising a first microcontroller 10 and a first motor controller 11, which is connected to the first microcontroller 10, is disposed in the housing 8, wherein these components form a main path for controlling, and possibly driving, the heart pump 5. The first motor controller 11 typically comprises at least one microprocessor.

Moreover, a second control unit comprising a second microcontroller 14 and a second motor controller 15, which is connected to the the second microcontroller 14, is disposed in the housing 8, wherein these components form an auxiliary path for controlling, and possibly driving, the heart pump 5. In some embodiments, it may also be provided that the first control unit and the second control unit are disposed in respective implantable housings. The second motor controller 15 typically comprises at least one microprocessor. The control units are configured to control operating parameters of the heart pump 5, such as a rotor speed and/or a motor current and/or a driving speed and/or signals for activating implanted sensors. For this purpose, for example, the microcontrollers 10, 14 can include stored characteristic map data based on which the operating parameters can be controlled as a function of input parameters, such as sensor data described hereafter. The microcontrollers 10, 14 provide the respective motor controllers 11, 15 with a control signal, for example a target motor speed and, in particular in the auxiliary operating state, directly provide a PWM or sinusoidal switching signal, for example via a digital interface. The motor controllers 11, 15 provide the current for the motor phases based on the control signal. Two phases at a time are cyclically energized in the process, and the back EMF is evaluated of one phase.

In addition, a switch comprising a switching unit 16, which is connected to the main path, the auxiliary path and, via the driveline 13, to the heart pump 5, is disposed in the housing 8. The switching unit 16 is configured to switch between a main operating state, in which the main path is used to control the heart pump, and an auxiliary operating state, in which the auxiliary path is used to control the heart pump. For this purpose, the switching unit 16, which is a transistor switch, for example, is configured to establish or disconnect a corresponding electrical connection between the heart pump 5 and the main path or the auxiliary path.

A switch controller 17 is connected to the switching unit 16, wherein the switching unit 16 and the switch controller 17 as well as connecting lines between these components form the switch. The switch controller 17 is designed as a logic circuit and connected to the first microcontroller 10. When the switch controller 17 detects a malfunction or a failure of the first microcontroller 10 and/or of the first motor controller 11, the switch controller 17 triggers a switch of the switching unit 16, so that the control device 7 switches from the main operating state into the auxiliary operating state. It may be provided, for example, that the switch controller 17 permanently or periodically receives an electrical signal from the first microcontroller 10 when the first microcontroller 10 and/or the first motor controller 11 function properly. The switch controller 17 can be configured to trigger a switch when this signal is absent.

The control device 7 moreover comprises an interface 18 for a wireless, transcutaneous communication with the extracorporeal control unit 3. The heart pump device 2, however, does not comprise any interfaces for a purely wired connection to the extracorporeal control unit 3 or other extracorporeal components. The interface 18 typically comprises a transmitter and receiver coil for inductively sending and receiving data and for receiving energy. In addition, or as an alternative, the interface 18 can comprise, for example, a transceiver including a transmitting or receiving antenna for wireless data transmission, for example in the RF range, between the control device 7 and the extracorporeal control unit 3. Via the interface 18, it is possible, for example, to program the first control unit and/or the second control unit and/or the switch controller 17 and/or to charge the power supply unit 9. The extracorporeal control unit 3 comprises an appropriately suitable interface 19.

The control device 7 is additionally configured to switch into the auxiliary operating mode by the application of a sufficiently strong magnet onto an outer side of the skin surface 4 in the region of the interface 18. For this purpose, for example, the first control unit and/or the second control unit and/or the switch controller 17 comprise a reed switch and a corresponding circuit. The reed switch is provided in addition to the switch 16.

The second control unit comprising the second microcontroller 14 and the second motor controller 15 has a considerably more compact design than the first control unit. When the heart pump device 2 is operated in the auxiliary operating mode, the rotor speed of the heart pump 5 established by the second control unit is constant and reduced compared to the main operating mode, so that the heart pump 5 is operated at a reduced power in the auxiliary operating mode. Moreover, the operating parameters of the heart pump 5 are also established based on sensor signals by the first control unit in the main operating state. The sensor signals, which can, for example, include a position of the rotor of the heart pump 5 and/or a plurality of other values, are detected by the different implanted sensors, which are not shown in the figure, and transmitted to the first control unit. The operating parameters controlled by the second control unit in the auxiliary operating mode, in contrast, are independent from this sensor data.

In the main operating state, the rotational speed of the heart pump can be set, for example, by the microcontroller 10 based on characteristic map data and/or the sensor data. The rotational speed can also be controlled dynamically, for example for an intake guard, and/or in a periodically varying manner for the generation of an artificial pulse.

In the auxiliary operating state, the microcontroller 10 typically sets a constant rotational speed. For this purpose, a measurement of the motor current can be used, for example. Thus, certain functions that are provided in the main operating state may be deactivated or not present in the auxiliary operating state, such as the intake guard and/or a periodic change of the rotational speed and/or the evaluation of the back EMF signal, so that, for example, a position of the rotor is not evaluated and/or considered in the auxiliary operating state.

Figure 2:
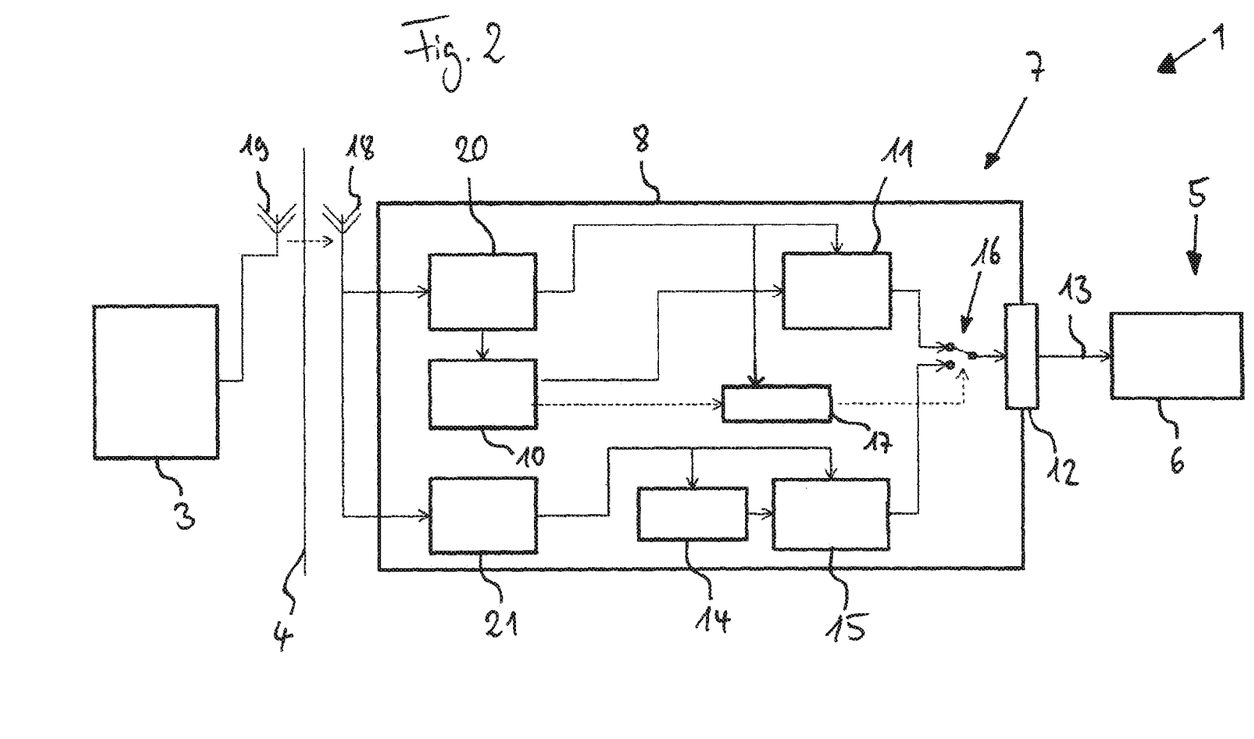
FIG. 2 shows a schematic view of a system according to a second embodiment.

In the example shown in FIG. 1, the power supply unit 9 supplies the microcontrollers 10, 14, the motor controllers 11, 15 and the switch controller 17 with electric energy. The energy for driving the heart pump 5 is supplied by an extracorporeal battery, which is not shown and which is inductively connected to the control device, and in particular to the interface 18. The exemplary embodiment of the system 1 shown in FIG. 2 differs in that the control device 7 comprises a main power supply unit 20, which is disposed in the housing 8 and connected to the first microcontroller 10 and the first motor controller 11, and an auxiliary power supply unit 21, which is likewise disposed in the housing 8 and connected to the second microcontroller 14 and the second motor controller 15. Recurring features are denoted by like reference numerals in this and the subsequent figures. Both the main power supply unit 20 and the auxiliary power supply unit 21 are rechargeable batteries and can be recharged via the interface 18. In the shown example, the switch controller 17, similarly to the first microcontroller 10 and the first motor controller 11, is supplied with energy by the main power supply unit 20.

Figure 3:
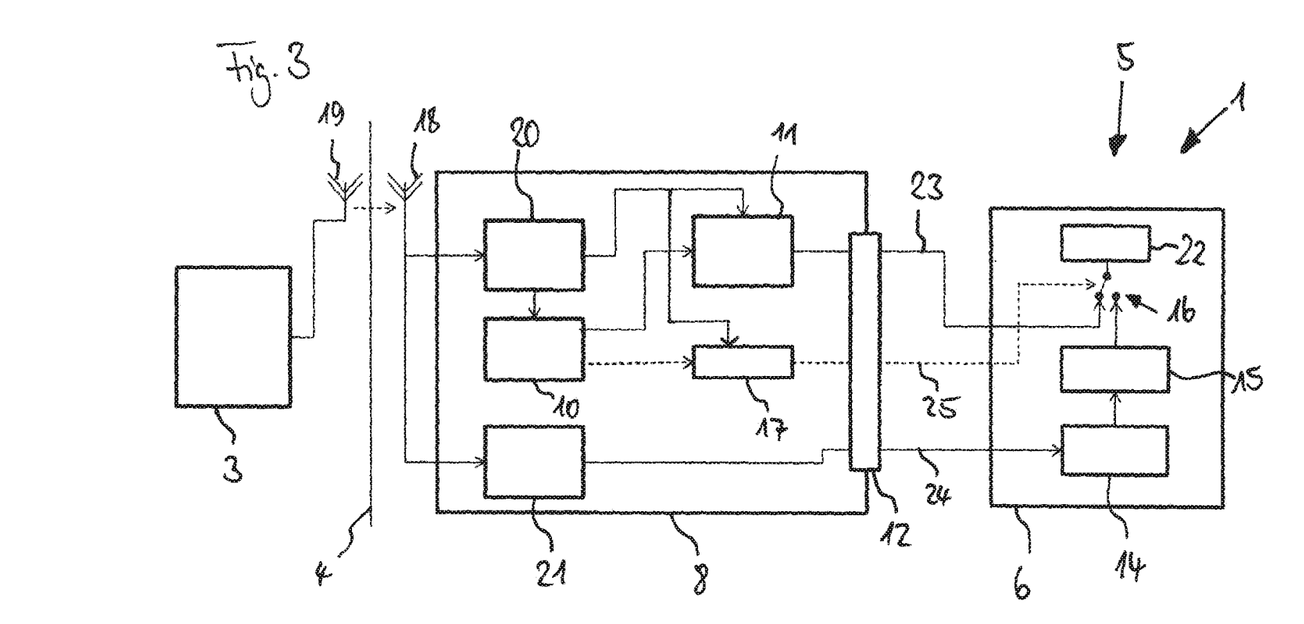
FIG. 3 shows a schematic view of a system according to a third embodiment.

FIG. 3 shows another exemplary embodiment of the system 1. This system 1 differs from the system described with reference to FIG. 2 in that both the switching unit 16 and the second control unit are disposed in the pump housing 6. In addition, FIG. 3 shows the motor 22 of the heart pump 5, which is electrically connected to the switching unit 16. The pump interface 12 in this case comprises three passages, these being a first passage for a driveline 23 for transmitting operating parameters from the first control unit to the switching unit 16, a second passage for a connecting line 24 between the auxiliary power supply unit and the second control unit, and a third passage for a connecting line 25 between the switch controller 17 and the switching unit 16.

Figure 4:
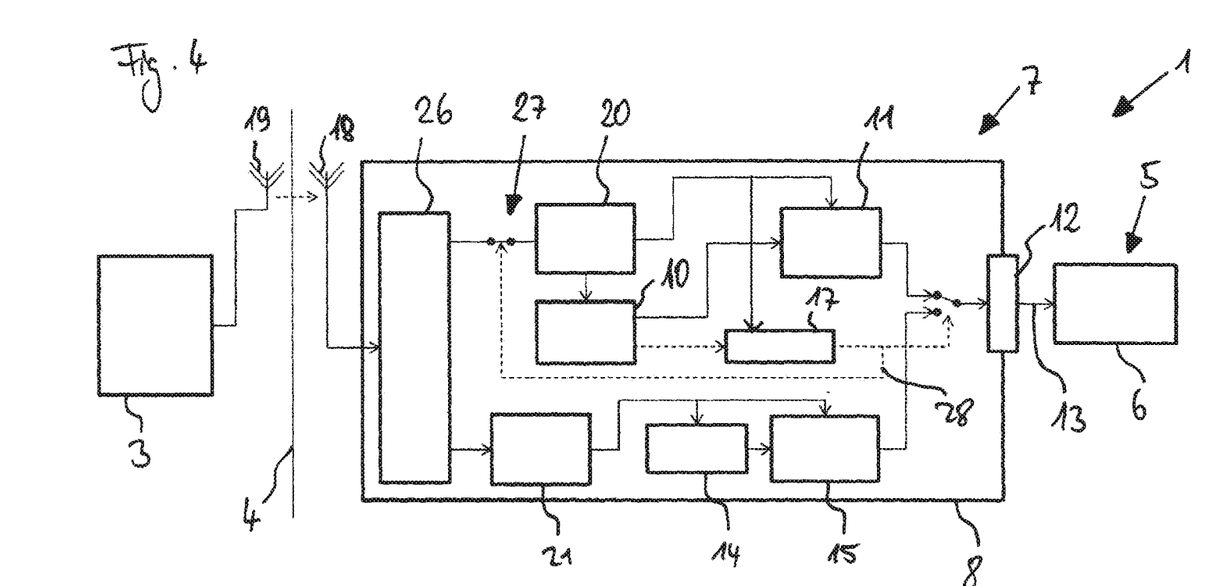
FIG. 4 shows a schematic view of a system according to a fourth embodiment.

FIG. 4 shows another exemplary embodiment of the system 1. This system 1 differs from the system shown in FIG. 2 in that a further rechargeable battery 26 is provided, which can be inductively charged via the interface 18 and supplies the main power supply unit 20 and the auxiliary supply unit 21 with energy. Moreover, the connection between the rechargeable battery 26 and the main power supply unit 20 is designed so as to be galvanically isolatable and/or de-energizable via a further switch 27. The further switch 27 can be controlled, via a schematically shown connection 28 between the switch controller 17 and the further switch 27, in such a way that the connection between the rechargeable battery 26 and the main power supply unit 20 is disconnected when the switch device 7 switches from the main operating state into the auxiliary operating state.

Only features of the different embodiments disclosed in the exemplary embodiments can be claimed combined with one another and individually.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, or N including any one element alone or the one element in combination with one or more of the other elements which may also include, in combination, additional elements not listed. Unless otherwise indicated or the context suggests otherwise, as used herein, "a" or "an" means "at least one" or "one or more."

The invention claimed is:

1. A control device configured for controlling an implantable heart pump, the control device comprising:
    an implantable first control unit, which in a main operating state is electrically connectable to the heart pump controlled by the control device, the implantable first control unit configured to control operating parameters of the heart pump;
    an interface electrically connectable to the first control unit for a wireless, transcutaneous data transmission and/or for a wireless, transcutaneous energy transmission between the first control unit and an extracorporeal control unit provided for extracorporeal use;
    an implantable second control unit, which in an auxiliary operating state is electrically connectable to the heart pump, the implantable second control unit configured to control the operating parameters of the heart pump, wherein the auxiliary operating state operates at a lower power than the main operating state;
    an implantable switch electrically connectable to the first control unit and the second control unit, the implantable switch configured to switch between the main operating state and the auxiliary operating state; and
    a single housing enclosing the first control unit, the second control unit, and the implantable switch, wherein the housing comprises a biocompatible material for an outer surface.

2. The control device according to claim 1, comprising an implantable power supply unit which is configured to supply both the first control unit and the second control unit with energy.

3. The control device according to claim 2, wherein an electrical connection between the power supply unit and the first control unit are disconnectable in the auxiliary operating state.

4. The control device according to claim 3, wherein the power supply unit is galvanically isolated.

5. The control device according to claim 1, comprising an implantable main power supply unit and an implantable auxiliary power supply unit, wherein the main power supply unit is configured to supply the first control unit with energy, and the auxiliary power supply unit is configured to supply the second control unit with energy.

6. The control device according to claim 5, wherein the power supply unit or the main power supply unit and/or the auxiliary power supply unit are wirelessly chargeable via the interface.

7. The control device according to claim 1, wherein the switch, the first control unit, and/or the second control are designed such that a switch from the main operating state into the auxiliary operating state is triggered via a wireless and transcutaneous connection.

8. The control device according to claim 7, wherein the switch, the first control unit, and/or the second control are designed such that a switch from the main operating state into the auxiliary operating state is triggered by an approach of a magnet.

9. The control device according to claim 1, wherein the outer surface of the housing comprises a biocompatible shell.

10. The control device according to claim 1, wherein the switch is configured to switch from the main operating state into the auxiliary operating state as a result of a malfunction and/or a failure of the first control unit.

11. The control device according to claim 1, wherein the first control unit is configured to send a switching signal to the switch, wherein the switch is configured to switch into the auxiliary operating state when receiving the switching signal and the switch is configured to maintain the auxiliary operating state when the switching signal is absent.

12. A system comprising:
    a control device for a heart pump; and
    a third control unit provided for extracorporeal use;
    wherein the control device comprises:
        an implantable first control unit, which in a main operating state is electrically connectable to the heart pump, the implantable first control unit configured to control operating parameters of the heart pump;
        an interface electrically connectable to the first control unit for a wireless, transcutaneous data transmission and/or for a wireless, transcutaneous energy transmission between the first control unit and the third control unit;
        an implantable second control unit, which in an auxiliary operating state is electrically connectable to the heart pump, the implantable second control unit configured to control operating parameters of the heart pump;
        an implantable switch electrically connectable to the first control unit and the second control unit, the implantable switch configured to switch between the main operating state and the auxiliary operating state, wherein the first control unit is configured to send a switching signal to the implantable switch which is configured to switch into the auxiliary operating state when receiving the switching signal, the implantable switch is configured to maintain the auxiliary operating state when the switching signal is absent, and the implantable switch is switchable from the main operating state into the auxiliary operating state in response to a malfunction and/or a failure of the first control unit; and
    wherein the heart pump is configured to be operated at a lower power in the auxiliary operating state than in the main operating state.

13. The system according to claim 12, wherein the heart pump is configured to be operated at a constant rotor speed in the auxiliary operating state.

14. The system according to claim 12, wherein operating parameters of the heart pump are controlled based on a sensor signal in the main operating state, and independently from this sensor signal in the auxiliary operating state.

15. A heart pump device, comprising a control device configured for controlling a heart pump, the control device comprising:
    an implantable first control unit, which in a main operating state is electrically connected to the heart pump controlled by the control device, the implantable first control unit configured to control operating parameters of the heart pump;
    an interface electrically connectable to the first control unit for a wireless, transcutaneous data transmission and/or for a wireless, transcutaneous energy transmission between the first control unit and an extracorporeal control unit configured for extracorporeal use;

an implantable second control unit, which in an auxiliary operating state is electrically connectable to the heart pump, the implantable second control unit configured to control operating parameters of the heart pump at a lower power than the main operating state; and an implantable switch electrically connectable to the first control unit and the second control unit, the implantable switch configured to switch between the main operating state and the auxiliary operating state, wherein the heart pump is electrically connected to the switch; and a single implantable pump housing enclosing the implantable first control unit, the implantable second control unit, and the implantable switch, wherein the single implantable pump housing comprises a biocompatible material for an outer surface.

16. The heart pump device according to claim 15, wherein the outer surface of the housing comprises a biocompatible shell.

* * * * *